(12) United States Patent
Shriver

(10) Patent No.: US 7,713,215 B2
(45) Date of Patent: May 11, 2010

(54) STEERING, PIERCING, ANCHORING, DISTENDING EXTRAVASCULAR GUIDEWIRE

(76) Inventor: Edgar L. Shriver, 3600 Mystic Pointe Dr., Apt 1715, Aventura, FL (US) 33180

( * ) Notice: Subject to any disclaimer, the term of this patent is extended or adjusted under 35 U.S.C. 154(b) by 0 days.

(21) Appl. No.: 12/012,086

(22) Filed: Jan. 31, 2008

(65) Prior Publication Data

US 2009/0198153 A1 Aug. 6, 2009

(51) Int. Cl.
A61B 5/00 (2006.01)
(52) U.S. Cl. .................................... 600/585
(58) Field of Classification Search ............... 600/433, 600/434, 585; 604/164.13
See application file for complete search history.

(56) References Cited

U.S. PATENT DOCUMENTS

| | | | |
|---|---|---|---|
| 243,396 A | 6/1881 | Pfarre |
| 419,926 A | 1/1890 | Chapman |
| 554,614 A | 2/1896 | Beyer |
| 623,022 A | 4/1899 | Johnson |
| 707,775 A | 8/1902 | Harris |
| 2,118,631 A | 5/1938 | Wappler |
| 2,211,976 A | 8/1940 | Hendrickson |
| 3,174,851 A | 3/1965 | Buehler |
| 3,416,531 A | 12/1968 | Edwards |
| 3,547,103 A | 12/1970 | Cook |
| 4,003,369 A | 1/1977 | Hielman |
| 4,516,972 A | 5/1985 | Samson |
| 4,569,347 A | 2/1986 | Frisbie |
| 4,676,249 A | 6/1987 | Arenas |
| 4,719,924 A | 1/1988 | Crittenden |
| 4,886,067 A | 12/1989 | Palermo |
| 5,040,543 A | 8/1991 | Badera |
| 5,060,660 A | 10/1991 | Gambale |
| 5,329,923 A | 7/1994 | Lundquist |
| 5,381,782 A | 1/1995 | DeLaRama |
| 5,477,856 A | 12/1995 | Lundquist |
| 5,599,326 A | 2/1997 | Carter |
| 5,664,580 A | 9/1997 | Erickson |
| 5,685,868 A | 11/1997 | Lundquist |
| 5,741,429 A | 4/1998 | Donadio |
| 5,762,615 A | 6/1998 | Weier |
| 5,957,903 A | 9/1999 | Mirzaee |
| 5,984,877 A | 11/1999 | Fleishhacker |
| 6,056,702 A | 5/2000 | Lorenzo |
| 6,500,130 B2 | 12/2002 | Kinsella |
| 2003/0195457 A1 | 10/2003 | LaFontaine |
| 2004/0073238 A1 | 4/2004 | Mackower |
| 2004/0116946 A1 | 6/2004 | Goldsteen |
| 2006/0111733 A1 | 5/2006 | Shriver |

*Primary Examiner*—Max Hindenburg
*Assistant Examiner*—Jonathan M. Foreman

(57) ABSTRACT

A steerable guidewire assembly for intravascular and extravascular movement includes a flexible tube with a distal and proximal end and a lumen therebetween with the distal end being biased to assume a curved shape, a stylet wire disposed in the lumen that can be advanced beyond the distal end of the flexible tube to create an extravascular pathway by piercing tissue, a wire with a shape memory of a knot to replace the stylet wire and anchor the guidewire and/or the wire on the pathway, multiple flexible tubes of increasing diameter that distend the extravascular pathway when advanced over each other, radiopaque and radiodense materials to create distinguishable dark and bright images on fluoro-unit screens, and mechanisms for conveniently controlling movement from outside the body are disclosed.

13 Claims, 5 Drawing Sheets

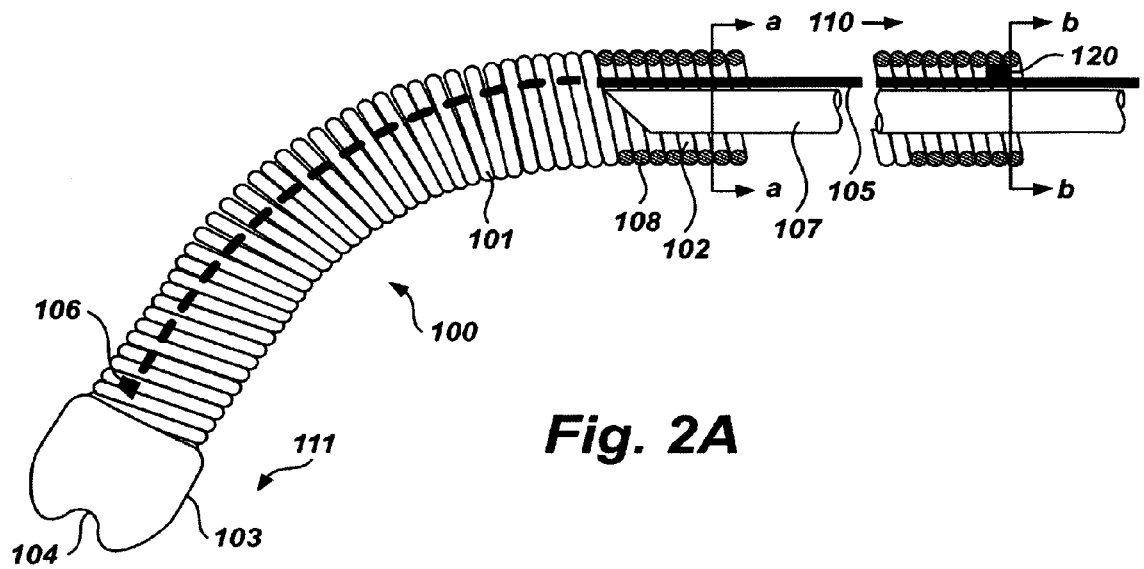
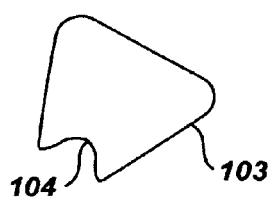 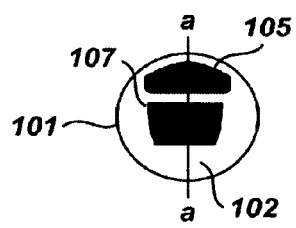 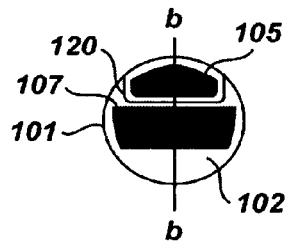
Fig. 2B    Fig. 2C    Fig. 2D

STEERING, PIERCING, ANCHORING, DISTENDING EXTRAVASCULAR GUIDEWIRE

CROSS-REFERENCE TO RELATED APPLICATIONS

This is a new invention by the inventor of the device disclosed in USPTO Pub. No. 0111733, pub. date May 25, 2006. The new invention is independent of the prior invention by the same inventor but may be used in combination with that invention as well as with other inventions.

FEDERALLY SPONSORED RESEARCH

Not applicable

SEQUENCE LISTING OR PROGRAM

Not applicable

BACKGROUND OF THE INVENTION

1. Field of the Invention

The field of the invention generally relates to guidewires, and specifically to a guidewire with the unique objects of piercing vascular walls, steering an extravascular pathway through surrounding tissue, anchoring at a site on the pathway created, distending the pathway, and showing the image of the guidewire and the vessel even when they overlap on the same fluro-unit screen.

2. Prior Art

Prior Art References:

|  | Year | Name |  |
|---|---|---|---|
| Patent Number |  |  |  |
| 243,396 | June 1881 | Pfarre |  |
| 419,926 | January 1890 | Chapman |  |
| 554,614 | February 1896 | Beyer |  |
| 623,022 | April 1899 | Johnson |  |
| 707,775 | August 1902 | Harris |  |
| 2,118,631 | May 1938 | Wappler |  |
| 2,211,976 | August 1940 | Hendrickson |  |
| 3,174,851 | March 1965 | Buehler |  |
| 3,416,531 | December 1968 | Edwards |  |
| 3,547,103 | December 1970 | Cook | 600/585 |
| 4,003,369 | January 1977 | Heilman et al. | 500/585 |
| 4,516,972 | May 1985 | Samson | 604/282 |
| 4,569,347 | February 1986 | Frisbie |  |
| 4,676,249 | June 1987 | Arenas et al. | 600/585 |
| 4,719,924 | January 1988 | Crittenden et al. |  |
| 4,886,067 | December 1989 | Palermo |  |
| 5,040,543 | August 1991 | Badera et al. |  |
| 5,059,183 | October 1991 | Semrad | 600/585 |
| 5,060,660 | October 1991 | Gambale et al. | 600/585 |
| 5,329,923 | July 1994 | Lundquist |  |
| 5,381,782 | January 1995 | DeLaRama et al. |  |
| 5,477,856 | December 1995 | Lundquist |  |
| 5,599,326 | February 1997 | Carter | 604/282 |
| 5,664,580 | September 1987 | Erickson et al. | 600/585 |
| 5,685,868 | November 1997 | Lundquist | 604/280 |
| 5,741,429 | April 1998 | Donadio, III et al | 216/8 |
| 5,762,615 | June 1998 | Weier |  |
| 5,957,903 | September 1999 | Mirzaee et al. |  |
| 5,984,877 | November 1999 | Fleischhacker, Jr. |  |
| 6,056,702 | May 2000 | Lorenzo |  |
| 6,500,130 | December 2002 | Kinsella, et al |  |
| Application Pub. No. |  |  |  |
| 0195457 | October 2003 | LaFontaine, et al |  |
| 0073238 | April 2004 | Makower |  |
| 0116946 | June 2004 | Goldsteen, et al |  |
| 0111733 | May 2006 | Shriver | 606/153 |

Percutaneous Catheter-Based Interventions

Atherosclerotic disease of the coronary, carotid and peripheral arteries accounts for more deaths among Americans than all other disease processes combined. Despite effective preventive care in the form of lifestyle, interventions, aspirin, statins, beta blockers, and ACE inhibitors, primary vascular interventions are required in more than 2 million cases in the United States each year. These vascular interventions are either surgical placements of bypass grafts around atherosclerotic occlusions or percutaneously introduced catheter-based devices for going through the occlusions. In percutaneous interventions a guidewire and/or catheter is inserted in the vascular system at a readily accessible location and advanced through vessel lumens as the vessels curve and branch in different directions until the distal tip of the guidewire is proximate a desired target site. These guidewires are specifically designed to stay within the vessels (intravascular) and not injure the vessel walls. The guidewire may be advanced through stenoses or partial occlusions in the vessel lumen such as plaque. This is done with a blunt end to avoid injury to the vessel walls. After the guidewire crosses a stenosis in this manner, an interventional device such as a catheter, balloon and stent is typically advanced over the guidewire to open the blockage and keep it propped open. Thus the guidewire establishes the intravascular pathway for the interventional catheter that follows. These catheter-based vascular interventions increase blood flow through blockages in coronary and peripheral arteries. In addition to these catheter-based interventions there are procedures for placing bypass grafts around the occlusions in coronary and peripheral arteries to increase blood flow. The only procedure for placing bypass grafts in use today is surgical. Bypass grafts last longer than catheter-based percutaneous procedures but the surgery is far more traumatic than percutaneous intervention. To make bypass grafts available without surgery several devices have been invented to place bypass grafts percutaneously by catheter-based methods rather than surgical methods. Since bypass grafts are placed outside the artery rather than inside (as balloons and stents are) the patent applications for placing bypass grafts percutaneously describe components for going outside the vasculature (extravascular) to deliver or guide the delivery of bypass grafts. Four patent applications for placing bypass graft percutaneously use the coronary arteries as application situations. And since the coronary arteries are located inside the pericardium, and the pericardium is filled with pericardial fluid, all the devices have only the object and means of moving through a transparent fluid medium. Peripheral arteries are in the lower extremities and are not surrounded by fluid but by muscle and other tissue. Thus prior art for placing coronary bypass grafts percutaneously is not emtirely applicable to peripheral arteries. About half the cases needing intervention are in peripheral arteries so the need is as great as in coronary arteries. But for bypass grafts to be placed around occlusions in peripheral arteries, a pathway must be established and distended in muscle tissue for a bypass graft—typically of several centimeters in length and about 3-8 mm in diameter. There is no prior art for a guidewire with the object of operating extravascularly in tissue nor any means for accomplishing the objects. And there are only 4 patent applications for percutaneously placing bypass graft in a transparent fluid medium found surrounding the coronary arteries. The means used in those inventions for operating in fluid will be described below and shown to be limited to transparent fluid media. In this event, it means there is no prior art to which the present invention for placing bypass grafts in peripheral arteries can be compared. But various means have been invented over more than a century to accomplish other objects with means similar to means used today. So these means will be discussed before describing the 4 patent applications that require extravascular travel through the fluid medium surrounding coronary arteries.

Objects and Means of Early Devices

The objects of the earliest devices with means recognizable as similar to those used in guidewires of today were for replacing parts in the body. There was no "guidewire" term but a "wire-wound coil" is found in early patents. In U.S. Pat. No. 243,396 by Pharre in 1881, he describes a coil of wire wound the way most guidewires are wound today, but on a mandrel of curved glass, and covered with vulcanized rubber or other material. The object of the device was to provide a curved replacement for a section of colon with the object of being more comfortable than the straight section of tubing previously available. The wire coil made a curved product possible and glass could be shaped to serve as a mandrel. Vulcanized rubber was a new material and may have been the only material in 1881 that made this invention possible. But today there are hundreds of materials that could be used—and are. In 1890 Chapman, in U.S. Pat. No. 419,926, describes a similar "catheter" device that includes covering the wire coil with celluloid rather than rubber. The early devices were not called guidewires because their object had nothing to do with guiding a catheter but were to substitute for body parts of similar shape. The objects for similar means had changed by 1938 when Wappler was issued U.S. Pat. No. 2,118,631 for changing the characteristics of a soft rubber uretheral catheter with what he called a "stylet." The object was not to replace a body part but to change the characteristics of a catheter that was inserted in the body and then removed. Thus the object was more like objects of today's guidewire than those of half a century before but still different. The "stylet" device had an outer layer of "wire-wound spring steel wire" just as many guidewires do today. Wappler called the device a "stylet" but it had blunt ends and no sharp point that is a characteristic of a stylet in today's medical terms. It had a more rigid tube inside the wire-wound coil that is similar to hypo tubes used today. This tube housed still another stiffening agent of a solid wire attached at each blunt tip. A safety ribbon in today's guidewires is very similar to that wire. But Wappler had no need for a safety wire. His object in using this wire and the other components of his "stylet" was only to achieve certain stiffness characteristics and not used in a way that would break the spring steel coil. As Wappler claimed, his device was " . . . to provide the requisite amount of rigidity for the primary purpose of facilitating entry of the catheter." So despite the similarity of means the object of those means and the objects of today are quite different.

Materials Limited in Early Devices Become Plentiful

The wire used in wire coils was generally described as "spring steel" up until the 1940's when the Naval Ordinance Laboratory developed NITINOL. Today's options include NITINOL, Eligiloy and other flexible metals for a coil and polymers and carbon fiber for hypotubes and other flexible catheters that can be used as guidewires. In some of the referenced patents, slots are cut in those flexible materials to enable them to bend more readily than they do with their inherent characteristics. No purpose is served in describing each of the slot patterns. It is sufficient to say that the slots are described as being in many patterns. It may be seen that a spiral helical cut in a solid tube can produce the same guidewire that is made by coiling a wire on a mandrel. With the abundance of materials and processes available today, essentially the same characteristics can be obtained by a variety of optional materials, processes, and treatments. There may be practical reasons for choosing a particular material or process that would be optimal for the number of units to be produced, i.e. economies of scale. But even that basis of selection could easily change during a patent period as could the practical experience in manufacturing one alternative over others. It is recognized by those experienced in the state of the art that the characteristics of flexible tubes can be effected by both process and material in their manufacture and that the same characteristics with respect to the certain objects can be obtained by different materials and manufacturing processes.

A guidewire is commonly made of a plurality of turns of a wire wrapped around a mandrel and less commonly of flexible tubes or tubes with various slot patterns cut to gain the same or similar characteristics a wound wire can provide. The mandrel used for manufacture of coiled wire is removed leaving a lumen in the guidewire which can have various "core" wires inserted in it. One such wire is called a "safety ribbon" with width greater than thickness, attached at the proximal and distal ends of the wire coil by brazing, soldering, welding, laser, adhesive, etc. This ribbon serves as a means of retrieving the coil from the body in the event the coil breaks at any point while under stress such as produced while crossing an occlusion. Core wires are typically made of high tensile strength stainless steel though other materials such as NITINOL and Eligiloy are also used.

Availability and Interchangability of Materials, Processes and Shapes

It is recognized that the term "wire" should not be taken as limiting a wire to a circular cross section, material or method of manufacture. A wire of any cross-sectional shape can be extruded but typically guidewire manufacturers of today use grinding to achieve different cross-sectional shapes. The most appropriate methods in the future may include processes different than those in typical use today to obtain particular wire shapes. For instance a ribbon wire used as a safety wire in many guidewires today are likely to be made of metallic materials such as stainless steel, tantalum, titanium, or a nickel-titanium alloy known as NITINOL but may be made of non-metallic material such as a polyurethane-based polymer that has shape memory similar to that of NITINOL. Likewise, methods of connecting materials include welding, brazing, soldering, adhesives and laser-based treatments. These are obvious alternative processes for making a connection called for in an invention. One or another process or material may be selected for an advantage based on such factors as production quantities but in terms of a patent they are obvious alternatives to anyone skilled in the art.

Making Guidewires Steerable and Rotatable

Guidewires are commonly made steerable within the branching vessels they navigate. The simplest means is by imposing a "J" bend or curve on the distal end by the manufacturer or by the operator prior to its introduction into the body. However this type of guidewire must be removed from the body to impart a different curvature and so the term "steerable" generally refers to devices in which the amount of curvature can be changed without removing the guidewire from the body. A steerable guidewire must be capable of being rotated to turn the plane of the curve in the direction desired by the operator. Rotating a guidewire is usually done with the aid of a clip clamped to it at the proximal end and is called "torquing." A wire-wound coil is not very effective in transmitting torque from the operator's proximal end to the distal end because the wire coil is likely to slightly increase in diameter to absorb the energy of rotation until it is great enough to result in rotation. This is typically described by operators as taking 180 degrees of rotation before the guidewire tip "snap rotates" 180 degrees, making all degrees between inaccessible. The inclusion of the safety ribbon attached at the proximal and distal ends of the coil provides for an increase in torque transfer between ends of the coil. The steering of the guidewire is sometimes accomplished by placing a curved wire in the guidewire lumen that causes the guidewire to approximate the same curvature and thus turn the plane of curvature in the direction the operator rotates the guidewire to move in. The stiff curved wire transfers the torque of rotation better than the wire-wound tube thus avoiding the problem of transferring rotational torque through the wire-wound coil. The object is to steer the guidewire in the lumen of one vessel into the lumen of another branch. This is typically described as a "tortuous" route between entry point and final destination when coronary arteries are the application area. The routes in peripheral arteries are much straighter and not described as "tortuous." A characteristic of current intravascular guidewires is a soft, flexible, lubricious distal section and blunt tip suitable for avoiding injury within a vessel. A coating of polytetrafloroethelene (PTFE) or other lubricious material over the blunt tip, distal end, several sections or all of the guidewire is typically used on most guidewires today so less force is required to move within the vessel and thus avoid injury to vessel walls.

Objects and Means of Steering Guidewires

In most steerable guidewires one of two means of curving the guidewire to steer it are used. One is a curved member in a straight flexible tube that imposes a curve on the distal segment of the guidewire when advanced into the segment. Kinsella utilizes this means. It has the effect of delivering more of the force in the direction of the curve but the amount of curvature is fixed by the amount placed on the curved wire during manufacture. With an object of piercing tissue a stiff stylet wire is needed to keep the guidewire (relatively) straight, and deliver the maximum force vector in line with the straight section of the guidewire not the curved section. A straight guidewire is stiffer than a curved one and more of the force applied at the proximal end will follow the straight path forward than will follow a curved path. Therefore the better means for accomplishing the object of piercing tissue is to have the guidewire straight rather than curved when it is being advanced extravascularly through tissue or at an acute angle of 30-45 degrees toward the wall of a vessel from inside or outside the vessel. The angle preferred for placing bypass grafts is about 30 to 45 degrees with respect to the artery. To satisfy this object, the stylet wire should produce curvature in the guidewire in about this range of angles when it is fully advanced in the guidewire with piercing point extended beyond the guidewire. However it is desirable for the guidewire to be further adjusted by pulling or relaxing the ribbon wire. It should be recognized that the stylet wire imposes its maximal stiffness on the guidewire when it is at the angle with respect to the vessel wall that is favored for placing the bypass graft. Pulling the ribbon wire stiffens the guidewire somewhat more than when the ribbon wire is relaxed. Therefore an object is for the guidewire to stiffen as the ribbon wire is pulled rather than stiffen as it is relaxed. That is, the sharp stylet wire should stiffen the coil and the pull wire stiffen it still more when piercing tissue. The guidewire described by Kinsella does not have the means of operating in this way. But neither does it have the object nor means of exiting the lumen to pierce tissue. But it does have a guidewire that straightens as it is pulled. This is different from most steerable guidewires that increase their curvature as their pull wire is pulled.

Object Determines Advantage in Pulling vs. Relaxing a Pull Wire

The means of curving a guidewire by pulling a wire that causes an inherent curvature in the distal section of the guidewire to increase when pulled is different from that of Kinsella and much more common. For instance invention U.S. Pat. No 4,719,924 by Crittendenden et al, in 1988 and later a variation in U.S. Pat. No. 5,381,782 by De La Rama et al in 1995 used a pull wire to cause the distal end to curve, not to straighten. That method creates the minimal stiffness at the distal end when maximally curved and relatively small stiffness when the guidewire is relatively straight (with the pull wire relaxed). That means satisfies the object of not damaging the vessel during intravascular travel but is contrary to the object of piercing the vessel wall for extravascular travel. What is an advantage of a means with respect to one object, is a disadvantage with respect to another object. Today's guidewires have the object of intravascular travel but do not aim at extravascular travel and generally do not use the means Kinsella used for that reason. The 1970 invention by Cook used a safety ribbon wire to straighten a curved section by pulling the coiled wire guidewire apart to lengthen the guidewire and thus tighten the fixed length of the safety ribbon attached to the guidewire at the proximal and distal ends. This method of increasing tension on the pull wire was awkward and Cook did not have the objective of maximal stiffness in the straight ahead direction that his device produced. Cook's object was to avoid piercing a vessel wall just like all of today's guidewires for intravascular travel. But his means was not the best for doing that. The object of all intravascular guidewires is to avoid piercing a vessel wall and that is more easily done with a pull wire that curves the guidewire rather than a pull wire that straightens it when pulled—because a straight coil is stiffer than a curved coil. But when the guidewire is used to pierce the vessel, and travel extravascularly through tissue, it is a disadvantage to have what is an advantage for moving intravascularly.

Object of Distinguishing Overlapping Images on Fluro-Unit Screens

In certain patent applications the terms "radiodense," "radiopaque," and "radiolucent" are used. The terms refer to the density of the materials used in percutaneous procedures performed in a cath lab and how they appear on fluroscopic screens of fluro-units. A dense material such as platinum will show as bright, a less dense material such as steel or iodine contrast will show as dark and still less dense material such as tissue will show a faint image, if any. Almost all procedures are conducted without bright images from radiodense materials. This is because two types of images that can be distinguished when overlapping in line-of-sight are not needed in intravascular use—and since dense materials like platinum are expensive and radiopaque materials are inexpensive, radiopaque images are common. If there were objects that required distinguishing images of things in the same line-of-sight, cost would not inhibit the use of a radiodense image for one and a radiopaque image for the other. This distinguishing of images is not needed for intravascular movement but is for extravascular travel. However when the guidewire moves extravascularly, the operator must have an image of the guidewire and the vessel to keep the guidewire on a parallel pathway. When both are overlapping in the same line-of-sight they cannot be distinguished if they are both dark images. Since the operator must have a means of seeing both elements in both side and plan views on the screens in order to navigate, the images must be made distinguishable and making a linear section of the guidewire or a radiodense material produces a bright image that can be seen in the same line-of-sight as a radiopaque dark image. That is not an object in prior art so this means of accomplishing it has not been needed for intravascular guidewire travel.

Object of Dilating Guidewire Pathway

In the peripheral arteries it is necessary to provide for increasing the diameter of the pathway for a bypass graft so it will fit within the (dilated) pathway for connection on both sides of the occlusion in the artery. This dilation is not an object of intravascular interventions as guidewires used for interventions move only inside vessels. They are not used to create pathways through tissue for placing bypass grafts and not used to dilate such pathways. In the 4 patent applications for placing bypass grafts on coronary arteries dilation is not an object because fluid needs no dilation and coronary applications are strictly fluid inside the pericardium. Since there is no need for dilation in percutaneous interventions there is no object and no means in prior art for providing dilation.

Shape Memory and Anchoring

A shape is placed on a wire made of shape memory material such as the metal NITINOL or the polymer oligodial during manufacture. But it returns to the simple wire shape until activated by heat or electrical stimulus to assume the "remembered" shape. The shape may be in the form of a knot or something else larger than the wire so that it provides an "anchor" to keep the wire from being pulled through, a hole the diameter of the wire. Intravascular guidewires have no object for being anchored in a vessel. Therefore anchoring by means of memory shape materials is not used in the guidewire prior art.

Guidewire Coatings

Using a lubricious material such as PTFE to coat all or part of intravascular guidewires is common, almost universal today. This means allows the guidewire to move with the application of less force thus helping to avoid damage to vessel walls. Moving a guidewire extravascularly through the resistance of tissue would be made easier by the same means, but since such an application has never been required (a fluid medium presents no resistance) there is no prior art for this use of a lubricious material.

Arteries in a Fluid Medium or a Tissue Medium in the Body

It is evident that the pericardial fluid surrounding the coronary arteries, veins, heart and aorta offers no resistance to the probe, guidewire, catheter, curved wire or object of any other description that moves extravascularly through this fluid medium. It is just as evident that the peripheral arteries in the legs are not in a fluid medium but are in muscle tissue. Therefore the means of moving extravascularly in the pericardial fluid are not applicable to peripheral arteries. The present invention is intended to apply to peripheral arteries. This requires extravascular pathways through tissue to percutaneously place bypass grafts on peripheral arteries. Thus the guidewire must have the objects of piercing vessel walls, moving through tissue surrounding peripheral arteries, re-entering the vessel to be anchored directly at the distal site of re-entry or anchored at a still more distal site reached by intravascular movement, another exit through a vessel wall, and piercing skin to anchor outside the body, distending the initial pathway to be large enough to accommodate a bypass graft, and providing distinguishable images of vessel and guidewire on fluro-unit screens even when both are in the same line-of-sight. There is no prior art with these objectives or means disclosed for accomplishing the unique objects. Thus, as stated previously, there are no direct comparisons to prior art.

Intravascular Objects vs. Extravascular Objects

The term "extravascular" is used here to refer to movement outside the vessel—as opposed to "intravascular" movement inside a vessel. Intravascular movement is the object of guidewires today with certain exceptions for percutaneous placement of bypass grafts in coronary applications that are now discussed. The first exception is a trivial case where percutaneous entry for intervention utilizes a hypodermic needle to pierce the skin and a thin layer of tissue to enter the vascular lumen. U.S. Pat. No. 3,547,103 by Cook in 1970 provides a description of this method of entry after which the guidewire invented by Cook is introduced into the vessel lumen through the lumen of the hypodermic needle. Though the object of this use of the hypodermic needle is similar to the object of other prior art to be discussed, the thickness of tissue to be pierced is so small and the path to be followed so straight that a device designed for a different object (introduction of fluid in the body through the skin) is convenient, usable and not patented. If there was a patent it expired before 1896 when Beyer's U.S. Pat. No. 554,614 described a modification to a syringe.

Four Prior Art Inventions with Extravascular Objects and Various Means

There are four prior art patent applications (referenced above) where extravascular travel is an object. All four have the overall object of placing bypass grafts percutaneously. Since bypass grafts are always placed outside the occluded vessel and connected proximally and distally with respect to the occlusion, this requires the establishment of an extravascular path. However all four used the coronary arteries for the application situation, and thus all extravascular movement was through the fluid medium within the pericardium where the heart and coronary arteries are located. Though all claimed to be applicable to other parts of the body, none provided the means for extavascular travel in a medium other than liquid. These patent applications for placing bypass grafts percutaneously are by LaFontaine, et al, 0195457, 10/2003, Makower, 0073238, 4/2004, Goldsteen, et al 0116946, 5/2006, and Shriver, 0111733, 5/2006. The components of each that provide the extravascular pathway between the proximal or distal sites through fluid are summarized as follows:

Mackower's component for passing through a vessel wall, at both the proximal and distal sites for the bypass on the coronary artery, travels extravascularly to an adjacent parallel coronary vein. He describes it as a sharp-tipped or semi-rigid cannula (probe) of stainless steel, NITINOL or polymer, capable of being inserted in the tissue alone—or with a relatively rigid wire, antenna, light guide or energy guide capable of being inserted in the tissue alone or with the sheath as support. Since the distance between a coronary artery and the parallel coronary vein is only a few millimeters the extravascular distance this cannula needs to travel between proximal and distal sites is a fraction of one percent of the extravascular distance a guidewire needs to travel between proximal and distal sites in a peripheral artery application. The path is straight between a coronary artery and the parallel coronary vein so the cannula does not need to be flexible as it does in a peripheral artery application. The cannula is straight and may or may not contain a "relatively rigid wire" as it is "sharp tipped." It should also be noted that the cannula passes through pericardial fluid, not tissue, to enter the coronary vein. Thus it is visible with or without fluro-unit screens. Because the veins are "tied off" at either end by an endovascular opening in the chest, direct visual means of viewing are available that are not available when using a guidewire extravascularly in peripheral arteries. Thus, though the object of this device includes extravascular travel, the object is not extravascular travel through tissue. Mackower does not limit his object to extravascular travel in a fluid medium—perhaps because he didn't perceive the limitation. Neither did he acknowledge the limitation of his object nor means to travel only a tiny distance though the limitation is obvious. There is virtually no similarity between this device and a guidewire for traveling extravascularly. The short rigid cannula cannot travel in a curving path for distances a hundred times greater than the length of the cannula. It is probably capable of piercing tissue but provides no way to distend tissue. Mackower has no object or means of viewing a coincident image of device and vessel on a fluro-unit screen but can depend on direct visual contact through endovascular openings. In short, though extravascular travel is an object of Mackower's invention, the objects and means of extravascular travel in the coronary artery application situation are not applicable in the peripheral artery situation.

Goldsteen, et al, use a tube or guidewire that must first cross the occlusion in a coronary artery to allow a stylet wire to emerge from the lumen through a side opening at a site just beyond the occlusion. The stylet wire is pushed through the vessel wall to extravascularly enter the interstitial space which is a fluid medium within the pericardium. It is essential that this be in a transparent fluid medium because the end of this wire is found by a fiber optic light and lens advanced through an arteriorotomy in the aorta at the proximal site. A gooseneck snare is also passed through the same proximal arteriotomy to snaring the short length of stylet wire outside the artery and drawing it back through the arteriotomy and intravascularly through the guiding catheter to the operator. This single wire is anchored by both proximal and distal ends being in the hands of the operator. This process of "fishing" for the short length of wire is done with visual light that requires a transparent fluid medium. The gooseneck loop must capture the end of a wire that has traveled extravascularly only a centimeter or so. This wire is a solid monofilament that presents a radiopaque image on a fluro-unit screen, but that image is not utilized. The object is to utilize a directly viewed visual image illuminated by visual light from fiber optics with light returning to the operator through the same fiber optics lens. This wire has no capability for being guided any more than to exit the artery wall at the distal site. The guidewire that delivers it to that site does not follow the wire extravascularly so no extravascular steering is possible. The "fishing" cannot be conducted in a tissue medium so the device has neither the means nor object of being applied in the peripheral artery situation. The Goldsteen device has received clinical trials but was apparently abandoned several years ago.

LaFontaine, et al, advanced a cutting catheter or cutting guidewire through an inverted bypass graft emerging from its connection at the proximal site on the aorta to the vicinity of its distal site on the coronary artery. The cutting tip of the guidewire/catheter is hollow like a hypodermic needle and may have a wire in the hollow lumen. It is used to go in a relatively straight path from aorta to coronary artery. The means of guiding it to the desired site is not described, but presumably by a radiopaque image on fluro-unit screens. The travel path must be essentially straight in order for the catheter to deliver sufficient force to cut through the artery. The distal end of this hollow needle catheter is surrounded by a collar with a beveled edge that enlarges the opening in the artery at the distal site to enable the bypass graft to enter the distal site. The bypass graft is turned inside-out to advance it through pericardial fluid to the distal site. A straight path through a fluid medium is required for this. A path through tissue would result in filling the guidewire/catheter with tissue. The path for a peripheral artery application is not straight but requires a 30-45 degree turn out of the proximal site in the artery and a 30-45 degree turn back in the artery at the distal site as well as a non-straight intravascular path. There is no object and no means of distending tissue with this device. There are no means of producing images of guidewire and vessel that are distinguishable on a fluro-unit screen as needed to keep the path from going off in random directions on a peripheral artery application. There is no object or means of providing an anchor as the bypass graft apparently is intended to enter the coronary artery as the cutting catheter makes the opening. It may be doubted that this can be accomplished even in the coronary artery application situation and there are no known tests with prototypes of the La Fontaine device as there are with the Mackower and Goldsteen devices. Thus the objects and means of the La Fontaine device may or may not be safe and effective in the coronary artery application but they clearly do not provide objects or means of accomplishing the objects required in peripheral artery applications.

Shriver uses a stylet wire with a screw tip and curve imposed by the physician to pass through an arteriotomy at the proximal site in the aorta through pericardial fluid to the coronary artery where it is twisted to anchor the screw at that site. The bypass graft is delivered in a catheter over this wire. This stylet wire is sharp enough to pass through tissue but it does not have the means or object of making multiple turns as required in turning out of the peripheral artery and turning again to re-enter it. It does not have the object or means of being steered without removing it from the body, for distending tissue, or for presenting a distinguishable image of wire and vessel as required in a peripheral artery application. Shriver, as did the others who used coronary arteries as application situations, said nothing about objects that limited the devices to coronary applications. On the contrary, all claimed generality to many other body areas. Shriver (and others) may have overstated the generality because of not adequately recognizing the difference with respect to other applications such as peripheral arteries. Now, in making an application to peripheral arteries it is clear what additional objects must be met by additional means that were not required in the fluid medium and in other specifics of the coronary application.

No Infringement on Prior Art by Same Inventor or others

It should be recognized that the present invention does not infringe on the prior art devices for placing bypass grafts, including the previous invention by Shriver, or on prior art such as stents, both of which may be used with the present invention. The guidewire of the present invention is separate, distinct and different from the guidewire disclosed in the prior patent application by the same inventor as well as different from all other prior art. It should be recognized that the present guidewire invention could be used with the non-guidewire components of any of the prior art devices under suitable licensing agreements. There are many cases of one invention being used with another. In the case of stents, the company owning the rights to stents needed a delivery system consisting of balloons, guidewires and catheters. They simply bought the company that owned the delivery system needed for stents.

3. Objects and Advantages

Accordingly, there is no prior art with the object or means of entering the body percutaneously, piercing tissue to create an extravascular pathway, anchoring the guidewire, presenting distinguishable fluoroscopic images of guidewire and artery, steering guidewire with one hand, and dilating that pathway to the size needed to place bypass grafts around occlusions in peripheral arteries thus providing the following unique advantages of the invention;

1. To provide a guidewire that will enter the vasculature of the body percutaneously, pierce vessel walls, pierce an extravascular pathway through tissue surrounding the vessels, pierce the vessel to move intravascularly and repeat these actions as the operator desires, including piercing the skin to leave the body at a remote distal site, and also to pierce occlusions, such as plaque, if desired.

2. To provide a guidewire that is steered both intravascularly and extravascularly by an operator outside the body.

3. A guidewire assembly for piercing tissue that delivers the maximum percentage of force applied at the proximal end to the piercing element on the distal particularly when creating a curved pathway through tissue. When the guidewire is creating a straight pathway through tissue, the maximum is easily obtained. When the path must be curved the percentage is reduced. The advantage of the present invention is to utilize a section of guidewire that is curved during manufacture and straightened as needed while being steered to create a pathway in the body. This delivers a higher percentage of the force than a straight guidewire that is manufactured straight and curved while being steered to create a pathway. Backpressure from the piercing element tends to make the curve more curved and thus losing a greater percentage of the force applied to the proximal end.

4. To provide a stylet wire and ribbon wire of width greater than thickness with thickness at right angles to the plane of curvature of the flexible tube as the means of resisting lateral movement outside the plane of curvature and thus maximizing the force vector in the direction the stylet wire point and/or guidewire assembly is directed. Any lateral movement causes backpressure from the piercing element to be directed in a vectorlateral to the force applied at the proximal end.

5. To provide the means of gaining an additional force vector in the direction desired by the operator through a chisel point stylet wire that moves in the direction opposite that of the force of tissues pushing against the face of the chisel point.

6. To provide a combination of means of delivering rotational torque in smooth increments from proximal to distal end of a flexible tube guidewire, without the snap rotation typical of wire-wound guidewires, so the guidewire will point in the precise direction the operator desires the plane of curvature to be directed in and thus move the guidewire in that desired direction when advanced. The means are an stylet wire that engages a hollow tip attached to the distal end of the flexible tube and thus delivering rotational torque from proximal to distal end, and by the ribbon wire that is attached at the distal end and passing slidably through a hanger fixed at the proximal end.

7. To provide increasingly large flexible tubes for advancing over the guidewire assembly as the means to dilate the pathway created by the guidewire assembly to the desired size.

8. To provide a replacement wire for the stylet wire and/or guidewire that will anchor the guidewire inside a vessel or outside the body.

9. To provide a means of distinguishing a dark radiopaque vessel from the bright radiodense guidewire on a fluro-unit screen even when the two images are overlapping or coincident in line-of-sight.

10. To provide a mechanism that provides a means for the operator to control the components of the guidewire assembly with one hand and deliver radiopaque contrast fluid into the flexible tube and thus the vessel.

11. To provide a ribbon wire that has a secondary function of recovering the guidewire if a coil breaks.

12. To provide a means of piercing occlusions such a plaque within vessels

SUMMARY OF THE INVENTION

The guidewire of this invention is a flexible tube with a distal end, proximal end, a lumen there between, a curved distal end, and an open distal tip. All or part of it may be coated with a lubricious material. A straight stylet wire of any cross section including a width greater than thickness, and tapered to a point on the distal end which may be a chisel point or pencil point is slidably disposed in the lumen with proximal end extending beyond the proximal end of the flexible tube even when the distal end is pushed through the open distal tip of the flexible tube to enable it to pierce any occlusion or tissue against which the flexible tube is directed by the operator. The hollow tip and stylet wire being of the same shape and slidably different in size cause rotational torque applied at the proximal end of the stylet wire to be directly transmitted to the distal end for turning the plane of curvature in the direction the operator desires the guidewire to move. The stylet wire also stiffens the curved section and tends to straighten it for piercing and but this is not the only means of changing the curvature of the flexible tube. A chisel point on the stylet wire can be rotated so that the pressure of passing through resistant occlusion or tissue imparts a force vector on the flexible tube opposite that imposed by the curvature, thus tending to produce straight movement when opposite the tendency imposed by the curvature, thus producing a straighter path. A ribbon wire of width greater than thickness may also be disposed in the lumen of the flexible tube which is attached to the distal end of the flexible tube on the side farthest from the center of the radius of curvature and extending proximally through a support loop on the distal end of the flexible tube and beyond the proximal end of the tube. When pulled the ribbon wire straightens the curve in the tube. When relaxed it allows the curve to decrease its radius of curvature to its inherent radius or to that which an extended stylet wire allows it to be. The ribbon wire also provides a safety function for withdrawing the flexible tube should a coil of wire break and contributes to delivering rotational torque from the proximal to distal end of the guidewire. A linear portion of the guidewire is made of radiodense material such as platinum to produce a bright image on a fluro-unit screen. Radiodense material such as contrast fluid may be injected through the lumen of the flexible tube. The object of the guidewire so constructed is to move outside a vessel lumen (extravavascularly) by piercing tissue and also to move intravascularly without piercing a vessel wall but to include piercing occlusions such as plaque in the vessel when the operator so desires. When an extravascular pathway is so established, additional guidewires of increasing diameter are provided to pass over the first guidewire thus distending the original extravascular pathway to the size desired. Further, a wire with a shape memory of a shape that constitutes a knot or anchor when activated may be substituted for the stylet wire to anchor on the extravascular pathway including a location outside the body. This wire may be of any diameter smaller than the stylet wire. A ribbon wire and stylet wire, of width greater than thickness, resist lateral bending outside the plane of curvature of the guidewire (sideways) while easily bending in the plane of the radius of curvature. This characteristic increases the force vector in the direction of guidewire travel while decreasing the (undesired) force vector in any lateral direction.

BRIEF DESCRIPTION OF THE DRAWINGS

FIG. 2A is a side view of the distal portion of a guidewire, a stylet wire, and a ribbon wire, with a radius of curvature imposed on the guidewire coil during manufacture in accordance with an exemplary embodiment of the present invention;

FIG. 2B is a cross-sectional view of FIG. 2 near the distal end of the guidewire;

FIG. 2C is a cross-sectional view of FIG. 2 near the proximal end of the guidewire;

FIG. 2D is a cross-sectional view near the proximal end of flexible tube shown in FIG. 2A at b-b;

Figure 1:
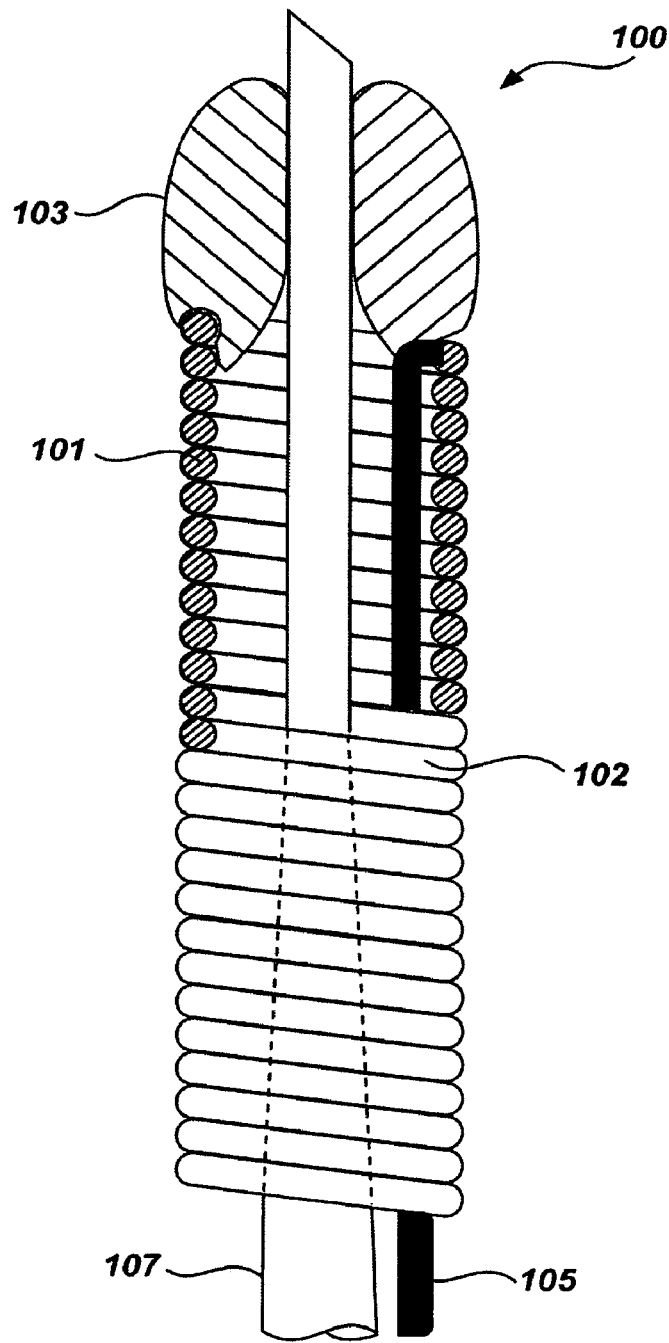
FIG. 1 is a side view of the distal portion of the guidewire with the radius of curvature made straight by the ribbon and stylet wire in accordance with an exemplary embodiment of the present invention.

KEY 100 guidewire
101 flexible tube
102 lumen
103 hollow tip
104 exit tunnel
105 ribbon wire
106 connection (ribbon wire and flexible tube)
107 stylet wire
108 sharp point (on stylet wire)
109 taper section (on stylet wire)
110 proximal direction
111 distal direction
112 vessel anchored replacement wire
113 control tube
114 finger loop (for middle finger)
115 connection (to control tube)
116 thumb loop
117 finger loop (for index finger)
118 short tube (for ribbon wire)
119 plunger tube
120 hanger
121 tightening screw (control tube to flexible tube)
122 tightening screw (short tube to stylet wire)
123 tightening screw (plunger to ribbon wire)
124 slot
125 support fixture
126 port
127 semi-circular tube
128 flexible bulb pump
129 inner core
130 skin anchored replacement wire
200 distending flexible tube
300 distending flexible tube (larger)
400 distending flexible tube (still larger)

DETAILED DESCRIPTION OF THE INVENTION

Having thus described the figures, methods in accordance with the present invention are now described with reference thereto. It should be understood that steps described for each process may be omitted or the order changed or performed simultaneously without deviating from the spirit or scope of the invention.

The following description should be read with reference to the drawings, in which the elements in different drawings are numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practice. Those skilled in the art will recognize that many of the examples provided have suitable alternatives which may be utilized now and in the future.

FIG. 1 is a side view of the distal portion of guidewire 100 in accordance with the present invention. Guidewire 100 constitutes a flexible tube 101 of metal, carbon fiber, plastic or other material with a proximal end 110 and distal end 111 and a lumen 102 therebetween, the preferred embodiment being a coil of wire of stainless steel, NITINOL, or other alloy. A curved shape is imposed on the distal section of flexible tube 101 which is not apparent in FIG. 1. This is because the combination of means for straightening the inherent curvature is forcing the radius of curvature toward infinite (straight). Flexible tube 101 will return to a curved shape once the means of straightening it are removed.

A hollow tip 103 is attached, by welding, brazing or other means, to the distal end of flexible tube 101 in such a manner as to allow the sharp point 108 of stylet wire 107 to pass through the hollow exit tunnel 104 and thus to a location exterior to flexible tube 101 and hollow tip 103. The hollow tip 103 is made of a material, metal, alloy, or plastic sufficiently stiff that exit tunnel 104 will not snag, bend or bind the distal end of stylet wire 107 passing through the exit tunnel 104 in slidable contact. The exterior shape of hollow tip 103 is not critical, being any shape from generally spherical, as shown here, to a beveled shape as individual physicians might prefer. Exit tunnel 104, is the same shape as the distal end of stylet wire 107 passing through except in the case where stylet wire 107 assumes a shape that is circular in cross section. Thus any rotational torque applied to the proximal end of stylet wire 107 is delivered to hollow tip 103 and to flexible tube 101 to which it is attached.

Stylet wire 107, made of stainless steel, NITINOL or other alloy, and of shape generally wider in width than in thickness in order to resist lateral movement, and to engage exit tunnel 104 in a way that delivers rotational torque. When stylet wire 107 is advanced into the curved section of flexible tube 101 this tends to straighten flexible tube 101 from its biased curvature. The distal end of stylet wire 104 has a sharp point 108 that may be conical or an oblique cross section. The oblique cross section has a face that receives a directional force vector against the face by passing through tissue whereas the conical shape imparts no directional vector as it passes through tissue. Stylet wire 104 is generally of greater cross section toward the proximal end than toward the distal end with a taper section 109 shown by dashed lines for transition in shape and/or size. Stylet wire 107 is in the same non-circular shape in cross section as exit tunnel 104, except in an alternative version of stylet wire 107 provided to operators when they desire to use the directional force on the face of sharp point 108 independently of rotating guidewire 100. This alternative version of stylet wire has a circular cross section where it goes through exit tunnel 104 of hollow tip 103 thus imparting no rotational vector to the hollow tip or flexible tube 101 to which it is connected. With this version of stylet wire 104, the sharp point 108, is obtained with an oblique transection which produces the face against which a force vector is produced in the direction opposite that face by pushing it through tissue and thus pushing the stylet wire in that direction. This force vector is in whatever direction the operator chooses to rotate stylet wire 107.

A ribbon wire 105, of the same or similar material as stylet wire 107, is in lumen 102 of flexible tube 101 and attached therto at connection 106, by a means similar to that for connecting hollow tip 103. The connection is made on the side of flexible tube 101 that is farthest from the center of the radius of curvature of flexible tube 101, and continuing proximally through the open proximal end of flexible tube 101. The radius of curvature of the guidewire as shown is infinite (straight) because the ribbon wire 105 is represented as being pulled by the operator as well as the stylet wire being advanced through the curved section. Pulling the ribbon wire straightens flexible tube 101 because it is connected on the outer circumference of the curved section and thus tending to increase the radius of curvature toward straight (as shown) when pulled. The stylet wire 107 cannot make the coil straight by itself but pulling the ribbon wire can make the coil straight without the aid of the stylet wire. When the sharp point 108 of stylet wire 107 is shaped as a pencil point, rather than as a chisel point, there is no force vector created in a lateral direction as there is no face to be pushed. The ribbon wire 105 and stylet wire 107 extend in the proximal direction 110 to the operator located outside the body where he has the choice of operating the guidewire with or without controls attached to the guidewire elements. The coil of wire has been shown in a "cut away" view to show the stylet wire and ribbon wire with its attachment. These elements are shown as dashed lines inside the lumen of the coil. The sharp point 108 of stylet wire 107, shown as an oblique transection here can be used with the stylet wire as circular or non-circular in cross section in exit tunnel 104 as can the conical point.

A section of one of the longitudinal members, such as ribbon wire 105 or the stylet wire 107 will have a radiodense material such as platinum or an alloy in place of the material described above is the primary material, in order for the guidewire to be seen on a fluorescent screen as bright.

FIG. 2A is a side view with the stylet wire withdrawn and the ribbon wire relaxed allowing flexible tube 101, which is biased to return to the curved shape imposed on it by the manufacture, to return to its curved shape. It may be noted that the ribbon is attached to the side of flexible tube 101 that is opposite the center of the arc of radius of curvature of guidewire 100. The radius of curvature can be controlled through the ribbon wire alone when stylet wire 107 is withdrawn from the curved section. Sharp point 108 is withdrawn from the curved section by the operator when guidewire 100 is moving inside the vessel (intravascularly) so as not to pierce the vessel wall accidentally. Those skilled in the art will appreciate that the curved portion may have any radius or curvature and any number of radii within the same plane of curvature, and that the method of connecting the ribbon wire and hollow tip to flexible tube 101 may be by soldering, brazing welding, adhesive bonding, and the method of cutting and shaping stylet wire 107 and ribbon wire 105 may be by abrasion, machining, grinding, laser cutting, water jet cutting or some other methods that may become practical in the future and thus replace methods in current use. The proximal end of the guidewire is shown which includes hanger 120 through which ribbon wire 105 slidably passes before going beyond the proximal end of flexible tube 101. Additional hangers 120 may also be placed at other intermediate points between the proximal and distal ends of flexible tube 101. Being so connected to flexible tube 101 causes ribbon wire 105 to impart any rotational vector applied to the proximal end of flexible tube 101 to the connection at the distal end of flexible tube 101.

FIG. 2B shows the hollow tip 103 in an optional beveled shape with exit tunnel 104.

FIG. 2C is a cross-sectional view of a distal portion of guidewire 100 shown in FIG. 2A at a-a. The cross-sectional size and shape of ribbon wire 105 and stylet wire 107 are typical shapes, generally rectangular in form at this location. It may be seen that stylet wire 107 is tapered here in the other dimension than that shown in FIG. 1. There may be a taper in either or both dimensions. The shapes are typically rectangular to resist movement lateral to the plane of the radius of curvature while increasing flexibility in the plane of the, radius of curvature. The shape of stylet wire 107 must be other than circular at the distal end to engage the shape inside the hollow tip 103 and exit 104 and thus impart rotational torque and circular in an alternate version that does not impart rotational torque.

FIG. 2D is a cross-sectional view near the proximal end flexible tube 101 shown in FIG. 2A at b-b. The hanger 120 which supports and slidably holds ribbon wire 105 thus causing torque exercised on the proximal end of flexible tube to be transmitted from proximal 110 to distal 111 ends of flexible tube 101. Hanger 120 may be placed at additional points than the one shown.

Figure 3A:
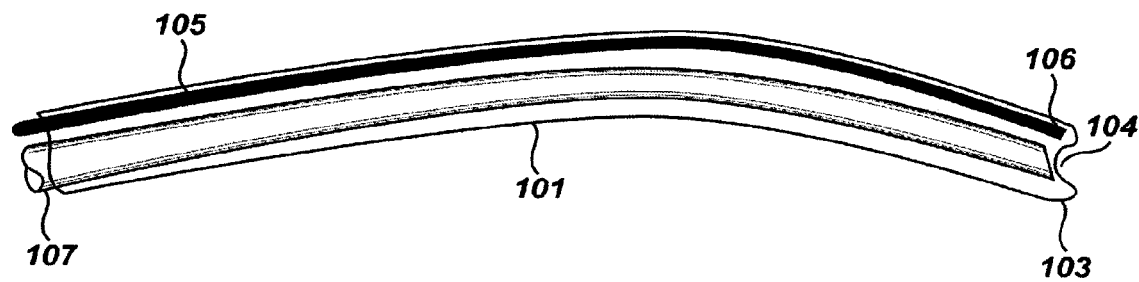
FIGS. 3A-3C is a side view showing schematically the three components of the guidewire acting together to straighten the curved section in three exemplary amounts and showing the stylet wire extended to pierce tissue or occlusions while the ribbon is pulled to draw the inherent curvature to be straight or an intermediate degree of curvature.

FIG. 3A is a schematic view of the guidewire with the stylet wire 107 extended to hollow tip 103 but not through exit tunnel 104, and with the ribbon wire 105 relaxed, thus producing the radius of curvature imposed by the stylet wire alone. The amount of curvature imposed by the stylet wire alone is generally about 45 degrees. The ribbon wire 105 can easily increase this to 30 degrees. This range is used because physicians prefer an angle between 30 to 45 degrees for placing bypass grafts on arteries.

Figure 3B:
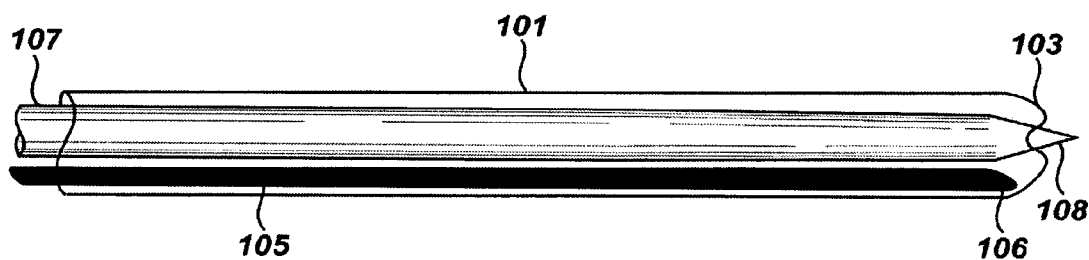

FIG. 3B A is a schematic view of the guidewire with the stylet wire 107 fully extended through exit tunnel 104 of the hollow tip 103 and the ribbon wire 105 connected distally at connection 106 pulled tightly by the operator thus making the guidewire straight. The sharp point 108 is shown as a conical point in this figure.

Figure 3C:
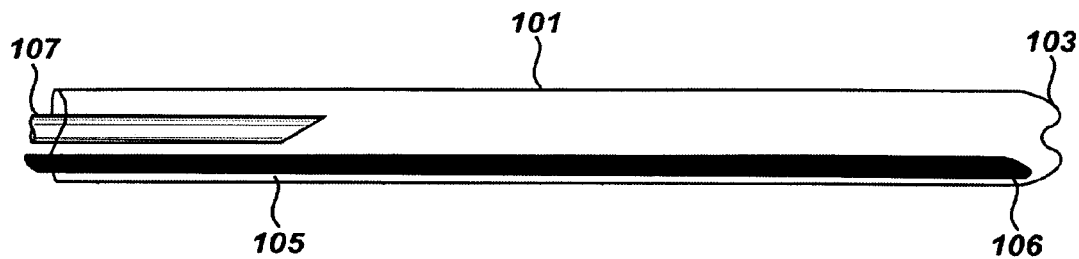

FIG. 3C is a schematic view of the guidewire with the stylet wire 107 withdrawn proximal to the curve and the ribbon wire 105 pulled tightly by the operator. With the stylet wire so withdrawn, the operator can achieve any radius of curvature between that of the inherent curve and an infinite radius which is a straight guidewire as shown.

Figure 4:
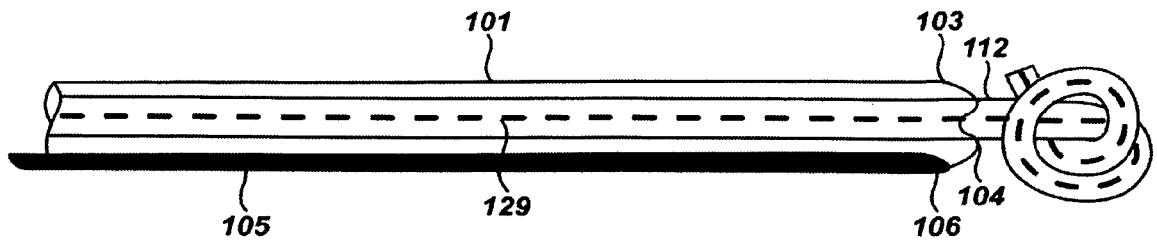
FIG. 4 is a view of a wire with shape memory activated for one type of wire that can be substituted for the stylet wire after the guidewire has accomplished its function.
Figure 5A:
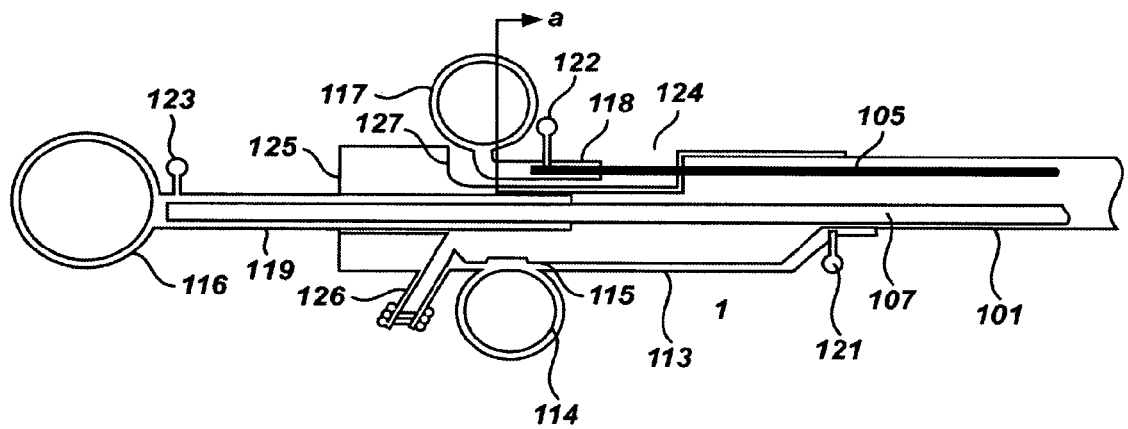
FIG. 5A is a schematic drawing of a component that can be manipulated by an operator to control the guidewire coil, stylet wire and ribbon wire more conveniently than by using fingers to grasp and control each separately.

FIG. 4 is a schematic representation of a replacement wire 112 inserted in the lumen of flexible tube 101 replacing stylet wire 107. Wire 112 has an inner core 129 running along its length inside wire 112. Replacement wire 112 wire may be of any cross-sectional shape or material but not larger than the stylet wire it replaces. It is made of shape memory material that provides a shape memory for a knot or other configuration that is larger than the diameter of the wire. Shape memory materials are shape shifted in the body by the application of heat slightly higher than body temperature or by electrical stimulation. An electrical conducing metal such as NITINOL has shape memory and an electrical insulation polymer such as oligodial has shape memory. When an electrical polymeric insulating material is used as replacement wire 112, an electrical conductor is used as inner core 129. This allows an electrical circuit to be produced for heating or stimulus of the shape memory material in replacement wire 112. The electrical circuit is between inner core 129 and the electrical conducting metal in either ribbon wire 105 or flexible tube 101. If an electrical conducting material is used for shape memory, it is used as the inner core 129 and an electrical insulating material is used as replacement wire 112. Those skilled in the art will appreciate that there are many such materials and memory shapes and the one shown as a knot in 112 is merely an example of one with a memory that assumes a particular knot shape when extended beyond the hollow tip 103 and stimulated to take the remembered shape inside the vessel lumen as an shape anchor. This anchor is placed at the distal site where the guidewire has entered a vessel. This anchor resists being taken out of the vessel while the pathway created is distended FIG. 5A is a schematic representation of a control mechanism the operator can use that is more convenient than manipulating each longitudinal element of the guidewire manually—without a tool. It requires only one finger to control each of the three controls individually rather than needing a thumb and finger to grasp each of the three elements of the assembly, two wires and one flexible tube—or having an assistant grasp one. Those skilled in the art will recognize that the physician operating the device may have preferences in the methods he or she uses and that the present configuration is only one of several that could be used, including none at all. A mechanism similar to that used in a large syringe has a control tube 113 with distal and proximal end and a lumen therebetween connected at 115 to finger loop 114 (for the middle finger). Control tube 113 is of a sufficient diameter to fit comfortably between the index and middle finger and reduce in diameter at the distal end to slidably fit over flexible tube 101 and is clamped thereto by tightening screw 121. On the opposite side of control tube 113 is finger loop 117 (for the fore finger) arranged in slot 124 such that it may be moved distally and proximally by one finger. Finger loop 117 is attached to a short tube 118 that slidably fits over ribbon wire 105 and it connected thereto by tightening screw 122. One finger is sufficient to pull or push finger loop 117 in slot 124 thus pulling or pushing ribbon wire 105. Slot 124 is isolated from the fluid in control tube 113 by semi-circular tube 127 attached to the body of control tube 113 at the four sides of the edge of slot 124. Thus fluid in control tube 113 is prevented from reaching slot 124. Short tube 118 is disposed in semi-circular tube 127 and may be pushed through a fluid tight opening in the distal end of semi-circular tube 127. A seal may be placed where short tube 118 exits semi-circular tube 127 if needed to make it fluid tight.

A third loop 116 (for the thumb) is attached to plunger tube 119 that slidably passes through support fixture 125 and slidably fits over stylet wire 107 and is connected thereto by tightening screw 121. Support fixture 125 reduces the proximal end of control tube 113 to the diameter of the plunger tube 119. The thumb and index finger can control the stylet wire and ribbon wire in a coordinated manner while the flexible tube is held steady by the middle finger. A port 126 in control tube 113 is connected to a source of contrast fluid that can be forced into the flexible tube lumen by squeezing flexible bulb pump 128 and delivered out the distal end of flexible tube 101. Any contrast fluid leaking between coils of wire in flexible tube 101 (rather than being ejected through the distal end or hollow tip 103) is of no consequence as that fluid is to mark the path of the vessel rather than mark a particular point. The material this control mechanism is made of is immaterial as it does not enter the body but plastic is less costly than stainless steel. But its similarity to the common large size syringe would suggest that using materials and production processes similar to those used to produce such syringes would simplify problems of production and use and be no more expensive than plastic. It should be understood that the construction of this control mechanism, being fluid-tight, would have seals placed as they are in a syringe.

Figure 5B:
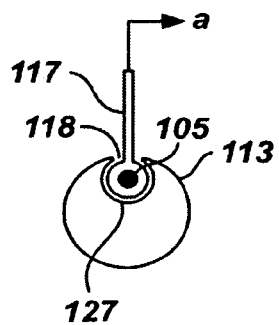
FIG. 5B is a cross-sectional schematic representation of a detail of the control mechanism shown in FIG. 5A.

FIG. 5B is a cross-sectional schematic representation of the detail shown in FIG. 5A

Figure 5C:
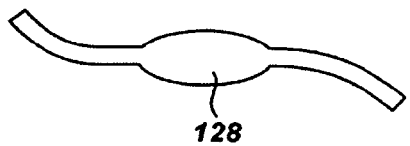
FIG. 5C is a schematic representation of a flexible bulb with connective tubes leading to a reservoir of contrast fluid and to the control mechanism shown in FIG. 5A.

FIG. 5C is a schematic representation of a flexible bulb pump 128 the operator squeezes to pump contrast fluid from a reservoir into the control tube through port 126.

Figure 6:
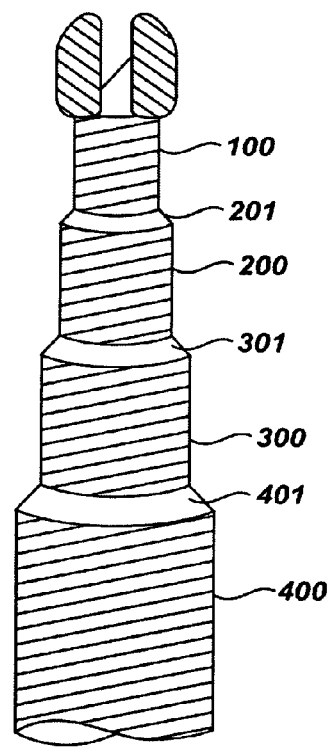
FIG. 6 shows three-coils of increasing diameter advanced concentrically over each other and the original guidewire to dilate the original pathway to successively larger diameters.

FIG. 6 is a schematic representation of successively larger distending flexible tubes 200, 300, and 400 being advanced over flexible tube 101. Each is tapered at its distal end as 201, 301, and 401 to displace tissue as with a knife blade. The action of a plurality of such distending guidewires of increasing diameter that slidably move over the guidewire of next smaller size is to distend tissue that guidewire 100 has passed through forming the pathway followed by each successive guidewire. This creates a pathway of sufficient size for the bypass graft and other device components delivering the graft to follow this pathway.

Figure 7:
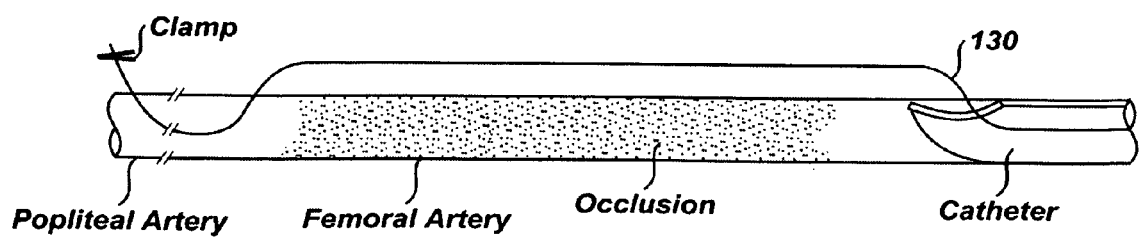
FIG. 7 is a schematic representation of a typical application situation for skin anchored replacement wire 130.

FIG. 7 is a schematic representation of a typical application situation in which guidewire 100 has created a pathway from the catheter making percutaneous entry to a vessel such as a peripheral femoral artery at a pre-selected proximal site, through the wall of the femoral artery and thus extravascularly through tissue around an occlusion to enter the femoral artery at a pre-selected distal site, then advanced intravascularly through the popliteal branch of the femoral artery to pierce the popliteal artery at a more distal pre-selected site and proceed extravascularly to create a more distal pathway and pierce the skin and exit the body (at the level of the knee). The guidewire is clamped there while the extravascular pathway is distended. Then a skin anchoring replacement wire 130 is anchored by a common clamp and drawn by the guidewire back through the created pathway to the place of percutaneous entry where another clamp is placed outside the body. The catheter for delivering a bypass graft utilizes the smaller wire to guide it through the distended pathway. This schematic representation shows skin anchoring replacement wire 130. An alternative anchoring location is in the femoral artery is at the pre-selected distal site on the femoral artery which requires the use of shape memory vessel anchoring replacement wire 112. Wire 112 is not shown in this figure.

Those skilled in the art will appreciate that still other embodiments may be made within the scope of claims attached. Changes may be made in details of shape, size, materials, arrangement of parts, and methods of manufacture without exceeding the scope of the invention. The term "wire" should not be taken as limiting the wire to a circular cross section, material or method of manufacture. A wire of any cross-sectional shape can be extruded but typically guidewire manufacturers of today use grinding to achieve different cross-sectional shapes. The most appropriate methods in the future may include processes different than those in typical use today to obtain the wire shapes described in this preferred embodiment. The flexible tube, ribbon wire and stylus wire may be made of metallic material such as stainless steel, tantalum, titanium, or a nickel-titanium alloy known as NITINOL, but may be made of non-metallic material and a linear portion of one will be made of platinum or other radiodense material. The anchoring wire may be made of a polyurethane-based polymer such as oligodial that has shape memory and is an electrical insulator, or of NITINOL or other metal alloy that has a memory shape and is an electrical conductor. Likewise, methods of connecting materials include welding, brazing, soldering and laser-based treatments that have advantages based on such factors as production quantities that may change with even slight changes in alloys used for prototypes.

What is claimed is:

1. A guidewire assembly providing the means of being introduced into the vasculature of the body percutaneously, steered by an operator located outside the body, moving intravascularly without injury to the vascular walls and, moving extravascularly, by piercing vascular walls and tissue surrounding said vasculature, thus creating extravascular pathways, and further enabling retrieval of said guidewire assembly should it break in the body, comprising,
   a. a flexible tube of metal, carbon fiber or other material in a coil or with cut slots having a proximal end and a distal end with lumen therebetween and with a section near said distal end being biased to assume a curved shape that returns to the original radius of curvature after being deviated and said lumen can carry contrast fluid,
   b. a stylet wire made of stainless steel, nickel titanium alloy or other alloy, disposed in said lumen, and having a distal end with a sharp point, proximal end extending beyond said proximal end of said flexible tube, and with said distal end being extensible into said curved shape and beyond said distal end of said flexible tube to pierce tissue or other substances,
   c. a ribbon wire disposed in said lumen of said flexible tube with a distal end attached to said distal end of said flexible tube on the side of said flexible tube farthest from the center of curvature of said curved shape, and continuing proximally beyond said proximal end of said flexible tube so as to be accessible to said operator to pull to increase the radius of curvature of said curved shape or relax to allow the said curved shape to return toward the un-deviated radius, and provide for retrieving said guidewire assembly should it break in the body,
   d. a hollow tip of metal or polymer with a proximal end and distal end and lumen therebetween, said proximal end being attached to said distal end of said flexible tube by such means as welding or brazing, said lumen being a slidably larger exit tunnel for said stylet wire and including a cross sectional shape like that of said stylet wire where it fits through said exit tunnel,
   e. at least one hanger for holding said ribbon wire having the same shape and slidably larger than the ribbon wire attached to the proximal end of the flexible tube;
   whereby said guidewire assembly can be steered by said operator in the direction said distal end of said flexible tube is pointed by means of (a) advancing said stylet wire in said curved shape thus tending to increase said radius of curvature, and withdrawing said stylet wire in the proximal direction thus allowing the distal end section to return to the biased curvature, (b) pulling said ribbon wire thus tending to increase said radius of curvature toward straight, and (c) rotating said stylet wire in said hollow tip, with both of similar cross section, efficiently delivers rotational torque from proximal end of said guidewire assembly to said distal end of said guidewire, thus rotating the plane of curvature of said curved section in the direction said operator wishes to steer said guidewire assembly, and further stiffening said curved section by advancing said stylet wire in said curved section and by keeping said stylet wire from twisting outside the plane of curvature thereby causing more of the force applied on said proximal end to be delivered in the desired forward direction, thus piercing said tissue more easily to create said extravascular pathway where percutaneously introduced grafts may subsequently be placed without surgery, and said ribbon wire providing a means of retrieving said guidewire assembly should said flexible tube break in said body.

2. The guidewire assembly of claim 1 further including,
a shape of said sharp point of said stylet wire being an oblique section which produces a face to said sharp point,
whereby a force lateral to the direction of movement on said face is exerted by movement through tissue.

3. The guidewire assembly of claim 1 further including,
a shape of said sharp point of said stylet wire being conical,
whereby movement through tissue exerts no force on said sharp point in any lateral direction with respect to the direction of movement of said sharp point.

4. The guidewire assembly of claim 1, further including,
a taper section between said distal end and said proximal end of said stylet wire with said taper section being ground, or otherwise modified during manufacture, to be smaller in cross-sectional size and/or of different in shape in cross-section in the section toward said distal end of said stylet wire than in the section toward said proximal end of said stylet wire,
whereby a different amount of stiffness is imparted to said guidewire assembly. by said stylet wire in said proximal, distal and taper sections.

5. The guidewire assembly of claim 1 further including,
a linear section toward said distal end of said guidewire assembly, such as said ribbon wire, being made of radiodense material,
whereby said linear section of radiodense material can be distinguished as a bright image on a fluro-unit screen, in contrast to a dark radiopaque image from a contrast filled vessel when the images are co-incident on said screen.

6. The guidewire assembly of claim 1 further including,
a spherical exterior shape on said hollow tip,
whereby said hollow tip of said spherical shape may be preferred by physicians who regard a patient in a particular case to benefit from use of this shape which may be safer during intravascular travel.

7. The guidewire assembly of claim 1 further including,
a beveled exterior shape of said hollow tip,
whereby said hollow tip may be preferred by physicians who regard a patient in a particular case to benefit from use of this shape which may be more effective during extravascular travel.

8. The guidewire of claim 1 further including;
a lubricious coating such as PTFE on all or part of said guidewire assembly including said hollow tip, said stylet wire and said ribbon wire,
whereby a given amount of force delivered at the proximal end of said guidewire assembly will move the distal end of said guidewire assembly more easily and movement of elements in slidable contact with each other will move with less force applied.

9. The guidewire assembly of claim 1, further including,
a shape of said stylet wire where generally width is greater than thickness from proximal to distal end but specifically at said distal end of said stylet wire,
whereby resistance is increased to lateral movement outside the plane of said radius of curvature of said guidewire assembly and thus a maximum percentage of the force of pushing said proximal end of said stylet wire is transferred to said distal end of said stylet wire to force said sharp point through tissue, and rotational torque applied to said proximal end of said stylet wire is maximally delivered to said hollow tip and thus to said flexible tube, thereby avoiding the problem of rotational energy being delivered intermittently as in a wire coil.

10. The guidewire assembly of claim 1, further comprising,
a shape at said distal end of said stylet wire of circular cross-sectional and slidably smaller than said exit tunnel of said hollow tip,
whereby rotational torque applied to said stylet wire, delivers essentially none of said rotational torque to said hollow tip and operator can utilize said lateral force on said face of said sharp point in steering said guidewire assembly without rotating said guidewire assembly.

11. The guidewire assembly of claim 1, further including:
a replacement wire for vessel anchoring that replaces said stylet wire in said guidewire assembly and anchors itself in a peripheral artery, comprising,
a. a replacement wire for vessel anchoring impressed with a shape memory larger than the vessel anchoring replacement wire diameter,
b. said vessel anchoring replacement wire replacing said stylet wire in said guidewire assembly,
c. an inner core of said the vessel anchoring replacement wire that extends throughout its length,
d. a vessel anchoring replacement wire of a polymer such as oligodial with a shape memory that shape shifts when heated to just above body temperature or by electrical stimulus,
e. said inner core of said vessel anchoring replacement wire being made of a metal that conducts electricity,
whereby said vessel anchoring wire with shape memory wire replaces said stylet wire in said guidewire assembly an anchors said guidewire assembly in a vessel such as a peripheral artery by being advanced through said lumen of said guidewire assembly which is in said pathway created by said guidewire assembly ending at the distal site on said vessel where said vessel anchoring replacement wire it advanced through the vessel wall and an electrical circuit is completed between said electrical conductor in said inner core and the metal of said ribbon wire and/or said flexible tube thus shape shifting said vessel anchoring replacement wire, thereby anchoring said replacement wire and said guidewire assembly to said distal site on said peripheral artery.

12. The guidewire assembly of claim 1, further including:
a replacement wire for vessel anchoring that replaces said stylet wire in said guidewire assembly and anchors itself in a peripheral artery, comprising,
a. a replacement wire for vessel anchoring impressed with a shape memory larger than the vessel anchoring replacement wire diameter,
b. said vessel anchoring replacement wire replacing said stylet wire in said guidewire assembly,
c. an inner core of said the vessel anchoring replacement wire that extends throughout its length,
d. a vessel anchoring replacement wire of a material that is an electrical insulator
e. said inner core of said vessel anchoring replacement wire being made of a metal such a nickel titanium alloy with a shape memory that shape shifts when heated to above body temperature or by electrical stimulus,
whereby said vessel anchoring wire with shape memory wire as said inner core replaces said stylet wire in said guidewire assembly an anchors said guidewire assembly in a vessel such as a peripheral artery by being advanced through said lumen of said guidewire assembly which is in said pathway created by said guidewire assembly ending at the distal site on said vessel where said vessel anchoring replacement wire it advanced through the vessel wall and an electrical circuit is completed between said electrical conducting metal in said inner core and the metal of said ribbon wire and/or said flexible tube thus shape shifting said vessel anchoring replacement wire, thereby anchoring said replacement wire and said guidewire assembly to said distal site on said peripheral artery.

13. The guidewire assembly of claim 1, further including:
a replacement wire for skin anchoring being of smaller diameter than said stylet wire and capable of being attached to said guidewire assembly after said guidewire assembly has created said pathway and pierced skin to exit said body at a pre selected distal site,
whereby said replacement wire for skin anchoring is drawn by said guidewire assembly through said pathway created by said guidewire assembly from a pre selected distal site on the said skin through the intravascular and extra vascular path of said guidewire assembly to the site of percutaneous entry where both ends of said replacement wire for skin anchoring are anchored by a common clamp, thereby providing a wire for guiding the delivery of a bypass graft on an occluded vessel such as a peripheral artery.

* * * * *